US00PP14736P2

(12) United States Plant Patent
Hofmann

(10) Patent No.: US PP14,736 P2
(45) Date of Patent: Apr. 27, 2004

(54) NEW GUINEA IMPATIENS PLANT NAMED 'FISNICS SWEET ORANGE'

(50) Latin Name: *Impatiens hawkeri*
Varietal Denomination: Fisnics Sweet Orange

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/452,980

(22) Filed: Jun. 3, 2003

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisnics Sweet Orange', characterized by its outwardly spreading and uniformly mounded plant habit; medium to tall growth habit; freely branching and freely flowering habit; very dark green-colored foliage; and large, nearly rounded, light and darker orange bi-colored flowers that are positioned above and beyond the foliage.

1 Drawing Sheet

Botanical classification/cultivar designation: *Impatiens hawkeri* cultivar Fisnics Sweet Orange.

BACKGROUND OF THE INVENTION

The present Invention relates to a new and distinct cultivar of New Guinea Impatiens plant, botanically known as *Impatiens hawkeri*, and hereinafter referred to by the name 'Fisnics Sweet Orange'.

The new Impatiens is a product of a planned breeding program conducted by the Inventor in Hillscheid, Germany and Galder, Gran Canaria, Spain. The objective of the breeding program is to develop new medium-sized Impatiens cultivars with an early to medium flowering response and large rounded flowers with attractive coloration.

The new Impatiens originated from a cross-pollination made by the Inventor during the spring of 1999 of a proprietary seedling selection of *Impatiens hawkeri* identified as code number K98-4090-10, not patented, as the female, or seed, parent with the *Impatiens hawkeri* cultivar Danharflm, not patented, as the male, or pollen, parent. The cultivar Fisnics Sweet Orange was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisnics Sweet Orange'. These characteristics in combination distinguish 'Fisnics Sweet Orange' as a new and distinct Impatiens cultivar:

1. Outwardly spreading and uniformly mounded plant habit; medium to tall growth habit.
2. Freely branching and freely flowering habit.
3. Very dark green-colored foliage.

4. Large, nearly rounded, light and darker orange bi-colored flowers that are positioned above and beyond the foliage.

Plants of the new Impatiens can be compared to plants of the female parent selection. In side-by-side comparisons conducted by the Inventor in Hillscheid, Germany, plants of the new Impatiens differed from plants of the female parent selection in the following characteristics:

1. Plants of the new Impatiens were slightly smaller than plants of the female parent selection.
2. Leaves of plants of the new Impatiens were darker green in color than leaves of plants of the female parent selection.
3. Flowers of plants of the new Impatiens were light and darker orange bi-colored whereas flowers of plants of the female parent selection were white and deep red bi-colored.

Plants of the new Impatiens can be compared to plants of the male parent, the cultivar Danharflm. In side-by-side comparisons conducted by the Inventor in Hillscheid, Germany, plants of the new Impatiens differed from plants of the cultivar Danharflm in the following characteristics:

1. Plants of the new Impatiens were slightly larger than plants of the cultivar Danharflm.
2. Flowers of plants of the new Impatiens were slightly larger and flatter than flowers of plants of the cultivar Danharflm.
3. Flowers of plants of the new Impatiens were light and darker orange bi-colored whereas flowers of plants of the cultivar Danharflm were solid orange red in color.

Plants of the new Impatiens can also be compared to plants of the cultivar Kimbu, disclosed in U.S. Plant patent application Ser. No. 09/765,323, abandoned. In side-by-side comparisons conducted by the Inventor in Hillscheid, Germany, plants of the new Impatiens differed from plants of the cultivar Kimbu in the following characteristics:

1. Plants of the new Impatiens were larger than plants of the cultivar Kimbu.
2. Plants of the new Impatiens had darker green-colored foliage than plants of the cultivar Kimbu.
3. Plants of the new Impatiens had larger flowers than plants of the cultivar Kimbu.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics Sweet Orange' grown in a container.

DETAILED BOTANICAL DESCRIPTION

The cultivar Fisnics Sweet Orange has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Sweet Orange.

Parentage:

*Female parent.*—Proprietary seedling selection of *Impatiens hawkeri* identified as code number K98-4090-10, not patented.

*Male parent.*—*Impatiens hawkeri* cultivar Danharflm, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D to 179D in color.

Plant description:

*General appearance.*—Outwardly spreading and uniformly mounded plant growth habit; medium to tall growth habit; freely branching habit, dense and bushy appearance; freely flowering. Moderately vigorous to vigorous.

*Crop time.*—From a rooted cutting, about 10 weeks are required to produce finished flowering plants in 12-cm containers.

*Plant height.*—About 20.5 cm.

*Plant diameter or spread.*—About 40 to 45 cm.

*Lateral branches.*—Quantity per plant: About 9 to 11. Length: About 5 to 16 cm. Diameter: About 5 to 7 mm. Internode length: About 4 to 6 cm. Texture: Smooth, glabrous. Color: 184A to 185A.

*Foliage description.*—Arrangement: Primarily in whorls. Length: About 13 to 14 cm. Width: About 4.5 to 5 cm. Shape: Elliptic. Apex: Acuminate. Base: Acute. Margin: Serrulate with ciliation. Texture: Smooth, very slightly rugose; glabrous. Color: Developing foliage, upper surface: Darker and more red than 139A, close to 187A. Developing foliage, lower surface: 187B. Fully expanded foliage, upper surface: Darker and more red than 139A, close to 187A. Fully expanded foliage, lower surface: 184A. Venation, upper surface: 53A. Venation, lower surface: 60A. Petiole: Length: About 1 cm. Diameter: About 3 mm. Texture: Smooth, glabrous. Color, upper surface: 53B to 53C. Color, lower surface: 53B.

Flower description:

*Flower type and flowering habit.*—Single, large, nearly rounded, light and darker orange bi-colored flowers. Freely and continuously flowering; usually about 6 to 8 flowers and flower buds per lateral branch. Flowers positioned above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 10 weeks after planting.

*Flower buds.*—Length: About 2.2 cm. Diameter: About 1.5 cm. Shape: Ovoid. Color: 41A.

*Flower length.*—About 7 to 7.2 cm.

*Flower width.*—About 6.4 to 6.6 cm.

*Flower depth.*—About 1 cm.

*Petals.*—Quantity: Five per flower, imbricate. Length: Banner petals: About 2.9 to 3.1 cm. Lateral and base petals: About 2.8 to 3 cm. Width: Banner petal: About 4.4 to 4.6 cm. Lateral and base petals: About 3.3 to 4.1 cm. Shape: Cordate. Apex: Weakly lobed. Base: Attenuate. Margin: Entire. Aspect: Mostly flat. Texture: Smooth; satiny. Color: When opening, upper surface: Ground color, 33D; banner petals, towards base and central stripes on lateral and base petals, 33A. When opening, lower surface: 41A to 41B. Fully opened, upper surface: Ground color, 29C; banner petals, towards base and central stripes on lateral and base petals, 33A to 33B; eye zone, 42A. Ground color closer to 29D with development. Fully opened, lower surface: 41A to 41B.

*Spur.*—Quantity: One per flower. Length: About 5 to 5.5 cm. Diameter: At apex: About 0.5 mm. At flower: About 2 to 3 mm. Aspect: Curved. Color: Towards base, 145C; towards apex, 51B.

*Peduncles.*—Length: About 5 to 6 cm. Diameter: About 2 mm. Texture: Smooth, glabrous. Strength: Strong, flexible. Color: Mostly 145C; with occasional overlay of 48C.

*Reproductive organs.*—Androecium: Stamen number: Five fused at anthers, hooded; filaments free. Anther length: About 5 to 6 mm. Anther shape: Obovate. Anther color: Close to 158A. Pollen amount: Moderate. Pollen color: 8D. Gynoecium: Pistil quantity: One per flower. Pistil length: About 6 mm. Stigma color: 53D. Style color: 53D. Ovary: Five-celled. Ovary color: 185A.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics Sweet Orange', as illustrated and described.

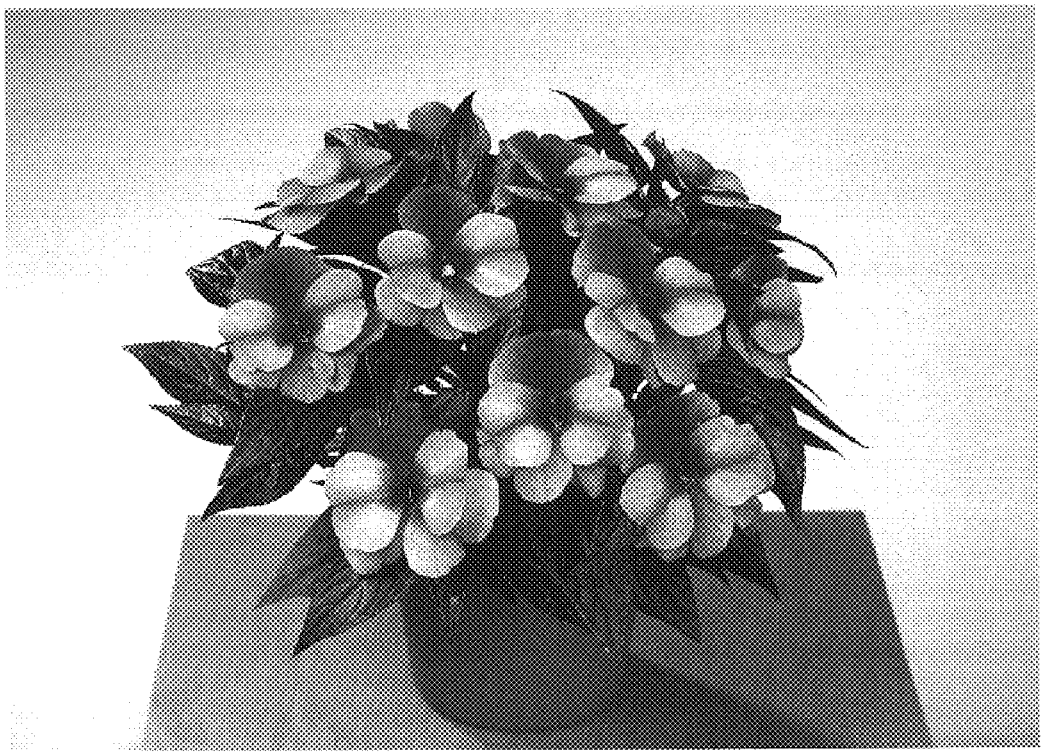

* * * * *